United States Patent [19]
Zhou et al.

[11] Patent Number: 5,912,348
[45] Date of Patent: Jun. 15, 1999

[54] METHOD OF MAKING ARYLAMINO TRIAZOLOPYRIDINES

[75] Inventors: Jiacheng Zhou, Wilmington; Lynette M. Oh, New Castle; Rajagopal Bakthavatchalam, Wilmington, all of Del.

[73] Assignee: DuPont Pharmaceuticals Company, Wilmington, Del.

[21] Appl. No.: 09/045,057

[22] Filed: Mar. 19, 1998

Related U.S. Application Data

[60] Provisional application No. 60/041,180, Mar. 21, 1997.

[51] Int. Cl.⁶ .................................................. C07D 471/04
[52] U.S. Cl. ................................................................ 546/117
[58] Field of Search ............................................. 546/112

[56] References Cited

PUBLICATIONS

Kelley et al, J. Med. Chem., vol. 38, pp. 4131–4134, 1995.

*Primary Examiner*—Bernard Dentz
*Attorney, Agent, or Firm*—Maureen P. O'Brien

[57] ABSTRACT

Method for making 4-arylamino-1-alkyl-[1,2,3]triazolo[4,5-c]pyridines by base-promoted isomerization of 7-alkylamino-3-aryl-[1,2,3]triazolo[4,5-b]pyridines.

5 Claims, No Drawings

METHOD OF MAKING ARYLAMINO TRIAZOLOPYRIDINES

This application claims priority from verified provisional application 60/041,180 filed Mar. 21, 1997.

FIELD OF THE INVENTION

This invention relates to preparation of 4-arylamino-1alkyl-[1,2,3]triazolo[4,5-c]pyridines by base-promoted isomerization of 7-alkylamino-3-aryl-[1,2,3]triazolo[4,5-b]pyridines. The 4-arylamino-1alkyl-[1,2,3]triazolo[4,5-c]pyridines are corticotropin releasing factor (CRF) receptor antagonists and are useful in treating abnormalities relating to CRF, such as psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress,

BACKGROUND OF THE INVENTION

Commonly-assigned U.S. provisional application 60/014,157, filed Mar. 27, 1996, discloses 4-arylamino-1alkyl[1,2,3]triazolo[4,5-c]pyridines and 7-arylamino-3-alkyl-[1,2,3]triazolo[4,5-d]pyrimidines and their use in treating CRF-related abnormalities. That application discloses that the 7-arylamino-3-alkyl-[1,2,3]triazolo[4,5-d]pyrimidines can be prepared by base-promoted isomerization of 3-aryl-7-alkylamino-[1,2,3]triazolo[4,5-d]pyrimidines according to the following scheme:

SUMMARY OF THE INVENTION

This invention is a method of making compounds represented by formula VI:

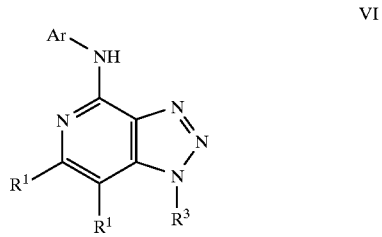

which comprises:

a. reacting a compound of formula I with a compound of formula II to produce a compound of formula III;

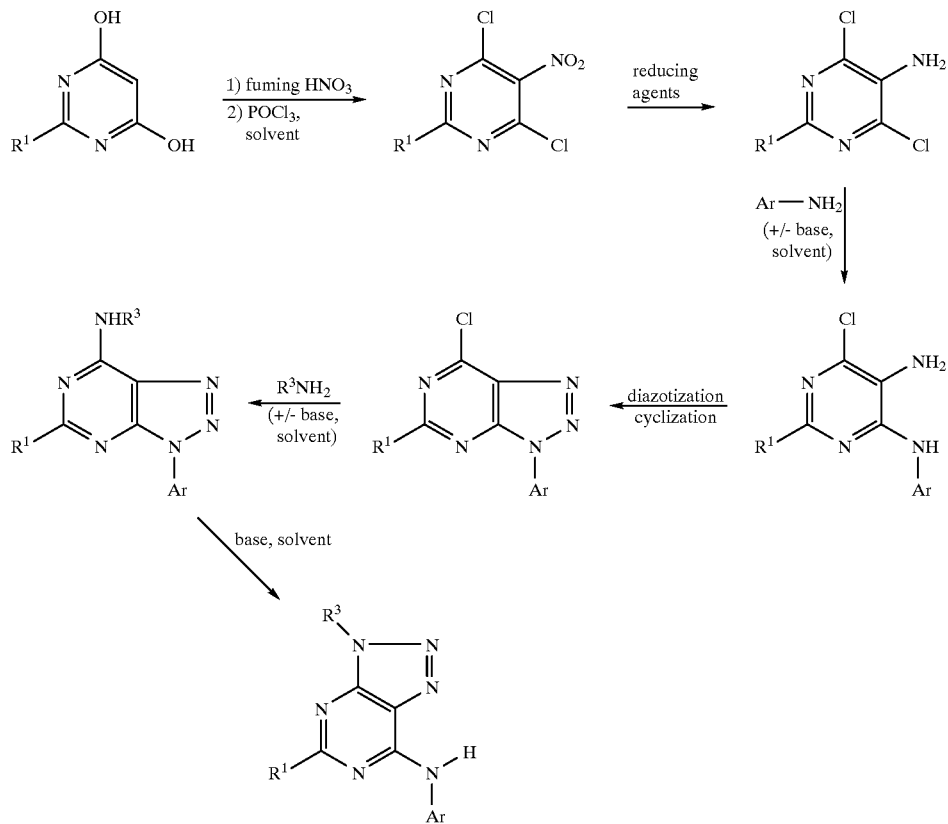

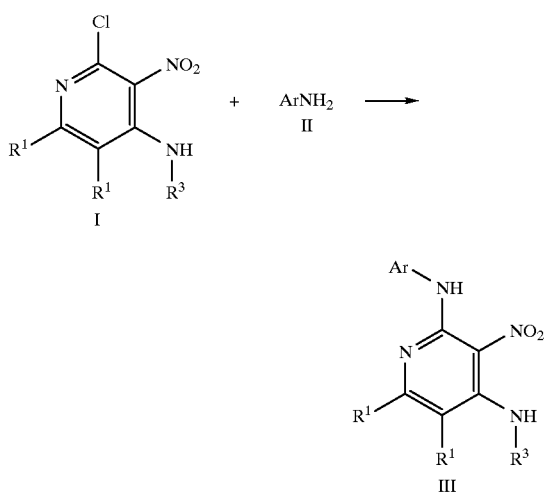

b. treating the compound of formula III with a reducing agent to produce a compound of formula IV;

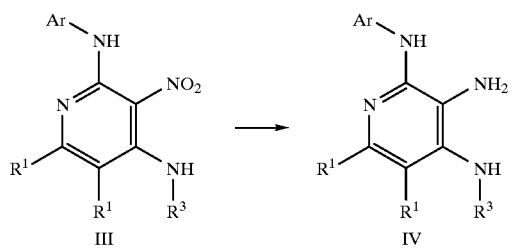

c. treating the compound of formula IV with diazotization and cyclization reagents to produce a compound of formula V or a mixture of a compound of formula V and a compound of formula VI;

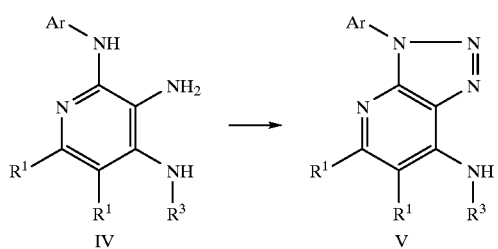

d. treating the compound of formula V or mixture of compounds of formulas V and VI with a base to convert the compound of formula V to the compound of formula VI

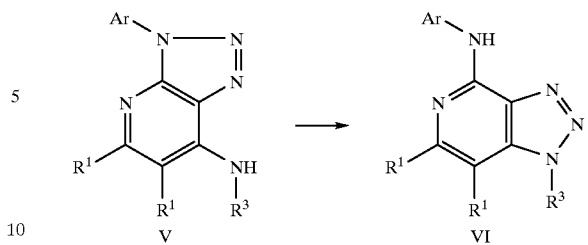

wherein in formulas I–VI, Ar represents an aryl group and $R^1$ and $R^3$ represent organic groups further defined below.

The invention also includes individual step d as a single step process.

The compounds of formula VI are corticotropin releasing factor (CRF) antagonists and are useful in treating abnormalities related to CRF, including psychiatric disorders and neurological diseases such as affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, shearing stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal.

DETAILED DESCRIPTION OF THE INVENTION

In formulas I–VI above, Ar, $R^1$ and $R^3$ have the following meanings:

Ar is independently selected at each occurrence from phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl and pyrazolyl, each optionally substituted with 1 to 5 $R^5$ groups;

$R^1$ is independently at each occurrence selected from H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH and —$S(O)_nR^{12}$;

$R^3$ is independently at each occurrence selected from H, $C_1$–$C_{10}$ alkyl, $C_2$–$C_{10}$ alkenyl, $C_2$–$C_{10}$ alkynyl, $C_3$–$C_8$ cycloalkyl and $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, —$CONR^6R^7$, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

$R^5$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —$CO(NOR^9)R^7$, $CO_2R^7$ and —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^8COR^7$, —$NR^8CO_2R^7$, —$COR^7$ —$OR^7$, —$CONR^6R^7$, $CO_2R^7$, —$CO(NOR^9)R^7$ and —$S(O)_nR^7$;

$R^6$ and R7 are independently at each occurrence selected from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-; or $NR^6R^7$ is piperidine, pyrrolidine, piperazine, N-methylpiperazine, morpholine and thiomorpholine;

$R^8$ is independently at each occurrence H or $C_1$–$C_4$ alkyl;

$R^9$ and $R^{10}$ are independently at each occurrence selected from H, $C_1$–$C_4$ alkyl, and $C_3$–$C_6$ cycloalkyl;

$R^{11}$ is independently at each occurrence selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is independently at each occurrence selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl, and indazolyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$; and n is independently at each occurrence 0, 1 or 2;

In a preferred embodiment, this invention is the above process wherein in formulas I through VI:

Ar is phenyl or pyridyl, each optionally substituted with 1 to 3 $R^5$ groups;

$R^1$ is independently at each occurrence selected from H, $C_1$–$C_4$ alkyl, halo, CN, $C_1$–$C_4$ haloalkyl, —$NR^9R^{10}$, —$OR^{11}$ and —$S(O)_nR^{12}$;

$R^3$ is independently at each occurrence selected from H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, —$S(O)_nR^{13}$, —$CO_2R^7$, —$NR^8COR^7$, —$NR^8CONR^6R^7$, —$NR^8CO_2R^{13}$, —$NR^6R^7$, aryl and heteroaryl, where the aryl or heteroaryl is optionally substituted with 1 to 3 substituents independently selected at each occurrence from $C_1$–$C_4$ alkyl, halo, cyano, —$OR^7$, —$S(O)_nR^7$, —$CO_2R^7$, —$NR^8COR^7$, —$NR^8CONR^6R^7$, —$NR^8CO_2R^7$, and —$NR^6R^7$;

$R^5$ is independently at each occurrence selected from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, —$NO_2$, halo, —CN $C_1$–$C_4$ haloalkyl, —$NR^6R^7$, $COR^7$ —$OR^7$, —$CONR^6R^7$, —$CO(NOR^9)R^7$, $CO_2R^7$ and —$S(O)_nR^7$, where $C_1$–$C_6$ alkyl, $C_2$–$C_6$ alkenyl, $C_2$–$C_6$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$, —$CO(NOR^9)R^7$ and —$S(O)_nR^7$;

$R^6$ and $R^7$ are independently at each occurrence selected from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is independently at each occurrence selected from H, $C_1$–$C_4$ alkyl, $C_1$–$C_4$ haloalkyl and $C_3$–$C_6$ cycloalkyl;

$R^{12}$ is $C_1$–$C_4$ alkyl or $C_1$–$C_4$ haloalkyl;

$R^{13}$ is independently at each occurrence selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-;

aryl is phenyl or naphthyl optionally substituted with 1 to 3 substituents independently selected at each occurrence from $C_1$–$C_4$ alkyl, halo, cyano, —$OR^7$, —$S(O)_nR^{12}$, —$CO_2R^8$, —$NR^8COR^7$, —$NR^8CONR^6R^7$, —$NR^8CO_2R^{12}$ and —$NR^6R^7$;

heteroaryl is independently at each occurrence selected from pyridyl, pyrimidinyl, triazinyl, furanyl, thienyl, imidazolyl, thiazolyl, indolyl, pyrrolyl, oxazolyl, isoxazolyl, pyrazolyl, triazolyl, tetrazolyl, or indazolyl, each optionally substituted with 1 to 3 substituents independently selected at each occurrence from $C_1$–$C_4$ alkyl, halo, cyano, —$OR^7$, —$S(O)_nR^{12}$, —$CO_2R^8$, —$NR^8COR^7$, —$NR^8CONR^6R^7$, —$NR^8CO_2R^{12}$, and —$NR^6R^7$; and n is independently at each occurrence 0, 1 or 2.

Step a of the process

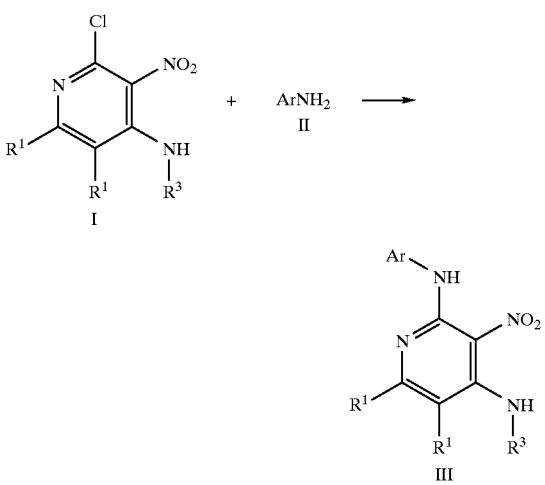

may be conducted neat, or in the optional presence of one or more solvents such as cyclic ethers such as tetrahydrofuran, dialkylformamides, ethylene glycol, 2-ethoxyethanol, halocarbons, alkanenitriles, toluene, or alkyl alcohols. The reaction can be conducted at room temperature or at elevated temperature up to the boiling point of the solvent employed, preferably about 25° C. to 70° C., for about 2 to 24 hours. Conditions which may facilitate the reaction include the optional presence of acids such as p-toluene sulfonic acid or benzene sulfonic acid, or bases such as alkali metal hydrides, trialkylamines, or alkali metal carbonates, or alkali metal bis(trimethylsilyl)amides wherein the metal can be sodium, lithium, or potassium.

Step b of the process

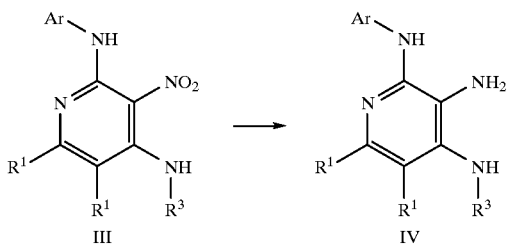

can be carried out by treatment of the nitro pyridine III with reducing agents such as, but not limited to, sodium dithionate, iron or zinc, or by catalytic hydrogenation (see: Larock, R. C. *Comprehensive Organic Transformations*, VCH Publishers, New York, 1989, 411). When using iron or zinc or catalytic hydrogenation, the reaction can be carried out in the presence of an acid, such as acetic acid or hydrochloric acid, in one or more solvents such as alkyl alcohols, acetonitrile or ethylacetate, at a temperature in the range of about 0° C. to 40° C., for about 0.5 to 3 hours. It is preferred to use sodium dithionate in the presence of a base such as sodium bicarbonate or ammonium hydroxide in one or more solvents such as tetrahydrofuran, dialkylformamides, dialkylacetamides, ethyl acetate, alkyl alcohols, halocarbons and alkane nitrites, at a temperature in the range of about 25° C. to 70° C., for about 0.5 to 3 hours.

Step c of the process

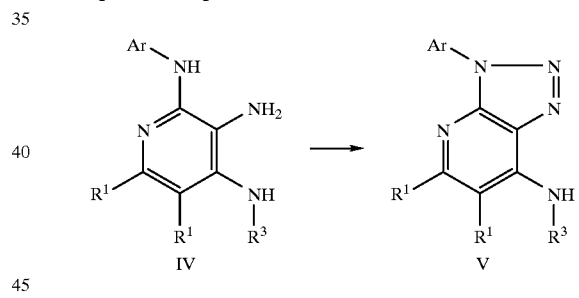

can be accomplished by diazotization and cyclization of the compounds of formula IV with an alkali metal nitrite in the presence of acid in water with or without an organic cosolvent such as halocarbons or cyclic ethers, at a temperature in the range of about 0° C. to 25° C., for about 0.5 to 2 hours. Alternatively, step c can be carried out with an alkyl nitrite such as isoamyl nitrite in the presence of any acid which forms a stable diazonium salt, such as fluoroboric acid or hexafluorophosphoric acid, in one or more solvents such as tetrahydrofuran, dialkylformamides, dialkylacetamides, ethyl acetate, alkyl alcohols, halocarbons and alkane nitriles, at a temperature in the range of about 0° C. to 25° C., for about 0.5 to 2 hours. Use of a metal nitrite results in mixture of isomers of formulas V and VI, for example in a ratio of V:VI of about 3:1. Use of an alkyl nitrite has been found to provide a regiospecific synthesis of the isomer formula V, for example in a ratio of V:VI of greater than 9:1. The isomer of formula V can be isolated from the isomer of formula VI before proceeding to step d, but this is not required.

Step d of the process

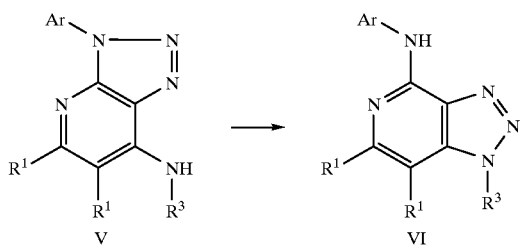

can be accomplished by treatment of the isomer of formula V or the mixture of isomers V and VI with a base such as an alkali metal hydride, alkaline earth metal hydride, or an alkali metal dialkyl amide in an inert solvent, such as tetrahydrofuran, a dialkylformamide, a dialkylacetamide, or 1-methyl-2-pyrrolidone, at temperatures ranging from about 0° C. to 200° C., preferably about 25° C. to 100° C., for about 1 to 24 hours.

If desired, the compound of formula VI can be reacted with a compound $R^4L$ to produce a compound of formula VII:

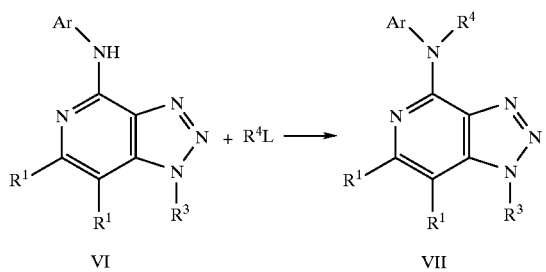

wherein

L is a suitable leaving group such as halo, methanesulfonate, p-toluenesulfonate, or triflate and $R^4$ is independently at each occurrence selected from H, $C_1$–$C_4$ alkyl, allyl and propargyl, where $C_1$–$C_4$ alkyl, allyl, or propargyl is optionally substituted with $C_3$–$C_6$ cycloalkyl and where $C_1$–$C_4$ alkyl is optionally substituted with, —$OR^7$, —$S(O)_nR^{12}$ or —$CO_2R^7$;

This reaction can be carried out in the presence of bases such as alkali metal hydrides, alkaline earth metal hydrides, alkali metal dialkyl amides in inert solvents such as dialkylformamides or dialkylacetamides at temperatures ranging from 0° to 200° C. Compounds of formula VI and VII have similar pharmacological activity and pharmaceutical utility.

Compounds of formulas VI and VII can be used in free base form or can be converted to pharmaceutically acceptable salts by reaction with acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is incorporated by reference.

EXAMPLE

Part A. 2-(2-Chloro-4,6-dimethyl)-phenylamino-4-(1,3-dimethoxy-2-propyl)amino-6-methyl-3-nitropyridine (3).

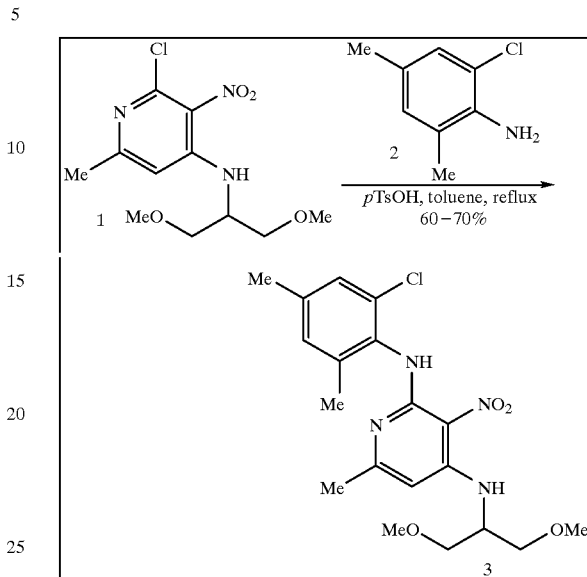

A suspension of p-toluenesulfonic acid monohydrate (6.84 g., 36 mmol., 1.2 equiv.) in toluene (150 mL) was warmed to reflux for 2 h, and the azeotropic mixture of water and toluene (50 mL) was removed during the course of the azeotropic distillation. After the mixture was cooled down to room temperature, 2-chloro-4-(1,3-dimethoxy-2-propyl) amino-6-methyl-3-nitropyridine hydrochloride salt (1, 9.8 g, 30 mmol) and 2-chloro-4,6-dimethylaniline (2, 4.68 g, 30 mmol, 1.0 equiv) were introduced to the reaction mixture, and the resulting reaction mixture was warmed to reflux for 6 h. The reaction mixture was then cooled down to room temperature, and was subsequently treated with saturated aqueous $NaHCO_3$ solution (100 mL) and tert-butyl methyl ether (TBME, 100 mL). The two layers were separated, and the aqueous layer was extracted with TBME (2×50 mL). The combined organic extracts were washed with saturated aqueous $NaHCO_3$ solution (50 mL), $H_2O$ (50 mL), and saturated aqueous NaCl solution (50 mL), dried ($MgSO_4$), and concentrated in vacuo. The residue was then directly purified by flash column chromatography ($SiO_2$, 15–30% EtOAc-hexane gradient elution) to afford the desired 3 (7.63 g, 12.26 g theoretical, 62.3%) as a yellow oil, which was solidified upon standing at room temperature in vacuo. The analytically pure material was obtained from recrystallization of the chromatographically pure 3 from TBME/hexane (1:5) as yellow crystals.

Part B. 3-Amino-2-(2-chloro-4,6-dimethyl)-phenylamino-4-(1,3-dimethoxy-2-propyl)amino-6-methylpyridine (4).

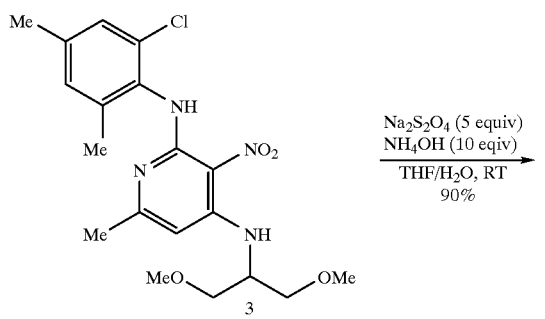

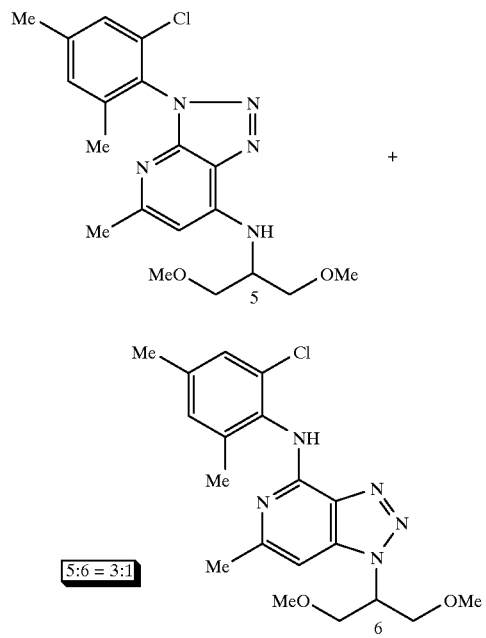

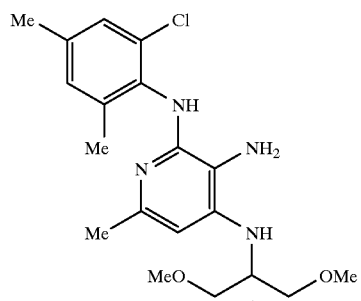

A solution of 3 (3.0 g, 7.34 mmol) in THF (10 mL) was treated with ammonium hydroxide (28–30% aqueous solution, 10 mL, 73 mmol, 10 equiv), Na$_2$S$_2$O$_4$ (6.38 g, 36.7 mmol, 5.0 equiv) and H$_2$O (10 mL) at room temperature under N$_2$. The resulting reaction mixture was then stirred at room temperature for 12 h before being treated with H$_2$O (20 mL) and EtOAc (50 mL). The two layers were separated, and the aqueous layer was extracted with EtOAc (4×20 mL). The combined organic extracts were washed with saturated NaHCO$_3$ aqueous solution (20 mL), H$_2$O (20 mL), and saturated NaCl aqueous solution (20 mL), dried (MgSO$_4$), and concentrated in vacuo. The residual oil was solidified upon standing at room temperature in vacuo to afford the desired g (2.5 g, 2.78 g theoretical, 90%) as yellow solids, which was found to be pure enough to go directly to the next reaction without further purification. The analytically pure product was obtained as yellow crystals by recrystallization of the crude material from TBME.

Part C. 3-(2-Chloro-4,6-dimethyl)phenyl-7-(1,3-dimethoxy-2-propyl)amino-5-methyl-[1,2,3]triazolo[4,5-b]pyridine (5) and 4-(2-Chloro-4,6-dimethyl)phenylamino-1-(1,3-dimethoxy-2-)propyl-6-methyl-[1,2,3]triazole[4,5-c]pyridine (6).

A solution of 4 (1.5 g, 4.0 mmol) in CH$_2$Cl$_2$ (10 mL) and HOAc (1.14 mL, 20 mmol, 5.0 equiv) at 0° C. under N$_2$ was treated dropwise with a solution of NaNO$_2$ (331 mg, 4.8 mmol, 1.2 equiv) in H$_2$O (3.0 mL). The reaction mixture was kept at 0–5° C. during the addition of the aqueous NaNO$_2$ solution. The resulting reaction mixture was then warmed gradually to room temperature for an additional 30 min before being treated with H$_2$O (20 mL) and CH$_2$Cl$_2$ (30 mL). The two layers were separated, and the aqueous layer was extracted with CH$_2$Cl$_2$ (2×20 mL). The combined organic extracts were washed with H$_2$O (20 mL), saturated aqueous NaHCO$_3$ solution (2×10 mL), H$_2$O (20 mL), and saturated aqueous NaCl solution (20 mL), dried (MgSO$_4$), and concentrated in vacuo. The oily residue was found to be a mixture of 5 and 6 (3:1, 1.4 g, 1.56 g theoretical, 90%) by $^1$H NMR, which was then separated by flash column chromatography purification (SiO$_2$, 15–30% EtOAc-hexane gradient elution) to afford 5 (967 mg, 62%) and 6 (320 mg, 21%). The analytically pure 5 was obtained by recrystallization of the chromatographically pure material from TBME-heptane (1:4).

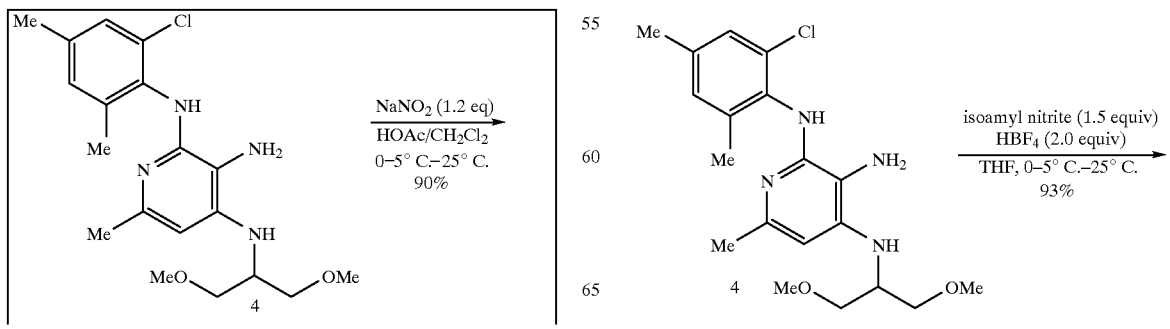

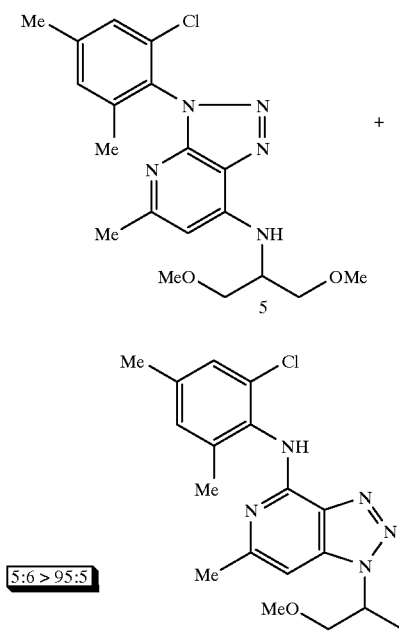

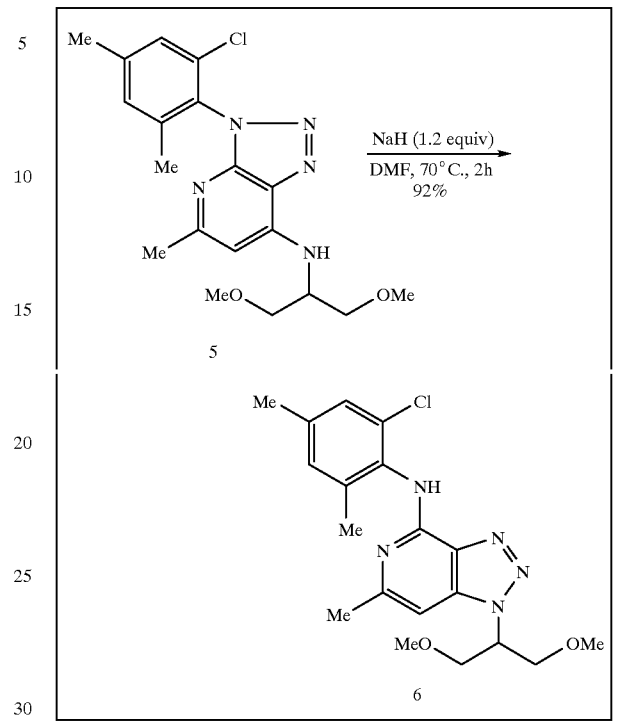

Method A:

A solution of 4 (1.5 g, 4.0 mmol) in THF (10 mL) was treated with HBF$_4$ (54% solution in ether, 1.3 g, 1.1 mL, 8.0 mmol, 2.0 equiv) at 0° C. under N$_2$, and the resulting mixture was then treated dropwise with isoamyl nitrite (643 mg, 0.74 mL, 6.0 mmol, 1.5 equiv). The reaction mixture was kept at 0–5° C. during the addition of isoamyl nitrite. The resulting reaction mixture was then warmed gradually to room temperature for an additional 30 min before being treated with H$_2$O (20 mL) and TBME (30 mL). The two layers were separated, and the aqueous layer was extracted with TBME (20 mL). The combined organic extracts were washed with H$_2$O (20 mL), saturated aqueous NaHCO$_3$ solution (20 mL), H$_2$O (20 mL), and saturated aqueous NaCl solution (20 mL), dried (MgSO$_4$), and concentrated in vacuo. The residual oil was found gradually solidified upon standing in vacuo at room temperature, which was found to be almost exclusively 5 (5:6>95:5) by $^1$H NMR. The crude solids were recrystallized from TBME-heptane (1:5) to afford pure 5 (1.45 g, 1.56 g theoretical, 93%) as off-white crystals.

Part D. 4-(2-Chloro-4,6-dimethyl)phenylamino-1-(1,3-dimethoxy-2-)propyl-6-methyl-[1,2,3]triazolo[4,5-d]pyridine (6).

A solution of 5 (195 mg, 0.5 mmol) in anhydrous DMF (2 mL) was cooled down to 0° C. and treated with NaH (60% disposition in mineral oil, 24 mg, 0.6 mmol, 1.2 equiv) under N$_2$. The resulting reaction mixture was gradually warmed to room temperature for 2 h before being warmed to 70° C. for 2 h. The reaction mixture was then cooled down to room temperature and treated with TBME (20 mL) and H$_2$O (20 mL). The two layers were separated, and the aqueous layer was extracted with TBME (2×10 mL) The combined organic extracts were washed with H$_2$O (20 mL), and saturated aqueous NaCl (20 mL), dried (MgSO$_4$), and concentrated in vacuo. The residual oil was solidified upon standing at room temperature in vacuo to afford pure 6 (178 mg, 195 mg theoretical, 92%).

Method B:

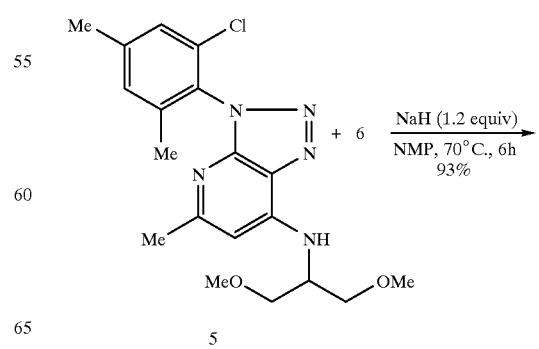

-continued

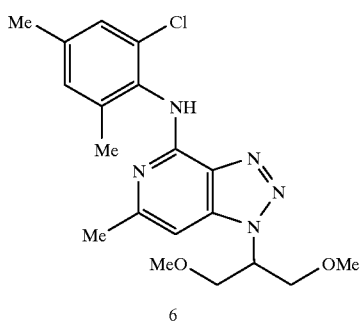

6

A solution of mixed 5 and 6 (5:6=3:1, 780 mg, 2.0 mmol) in anhydrous 1-methyl-2-pyrrolidone (NMP, 8 mL) was cooled down to 0° C. and treated with NaH (60% disposition in mineral oil, 96 mg, 2.4 mmol, 1.2 equiv) at 0° C. under $N_2$. The resulting reaction mixture was stirred at 0° C. for 10 min before being warmed to room temperature for overnight. The isomerization was found to be very slow at room temperature, so the reaction mixture was further to warmed to 70° C. for 6 h before the isomerization was completed. The reaction mixture was then cooled down to room temperature and treated with TBME (20 mL) and $H_2O$ (20 mL). The two layers were separated, and the aqueous layer was extracted with TBME (2×20 mL). The combined organic extracts were washed with $H_2O$ (2×20 mL), and saturated aqueous NaCl (20 mL), dried ($MgSO_4$), and concentrated in vacuo. The residual oil was solidified upon standing at room temperature in vacuo to afford pure 6 (726 mg, 780 mg theoretical, 93%).

Utility

Compounds of formulas VI and VII have utility in the treatment of abnormalities in humans and other mammals which are associated with corticotropin releasing factor and/or a receptor for corticotropin releasing factor. These disorders includes affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression, dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, shearing stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal. Also included are numerous other disorders such as those mentioned in the disclosure of WO95/33750, at pages 7 and 8, which is incorporated herein by reference.

Compounds of formulas VI and VII can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

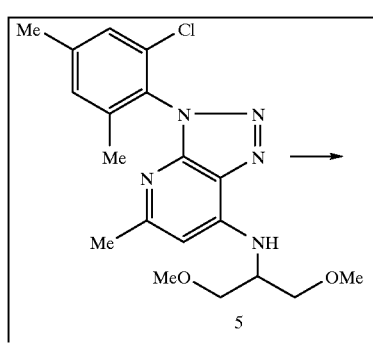 → 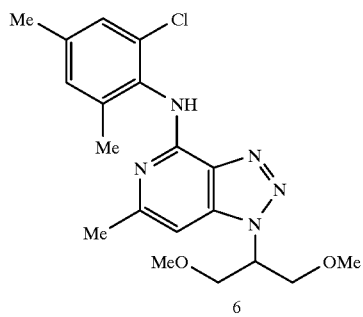

We claim:
1. A method of making a compound of formula VI:

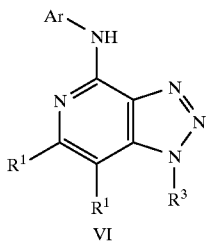
VI which comprises:

a. reacting a compound of formula I with a compound of formula II to produce a compound of formula III;

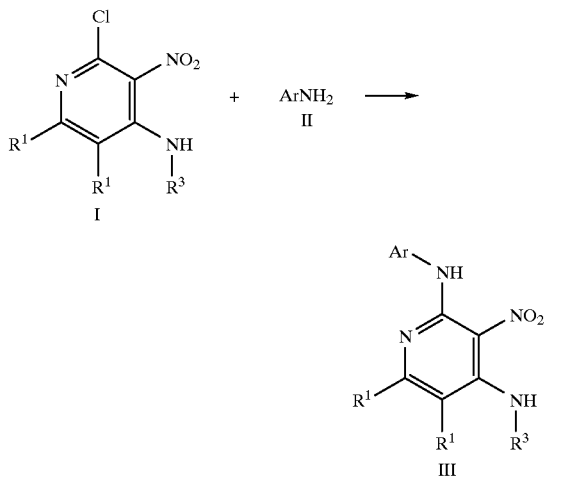

b. treating the compound of formula III with a reducing agent to produce a compound of formula IV;

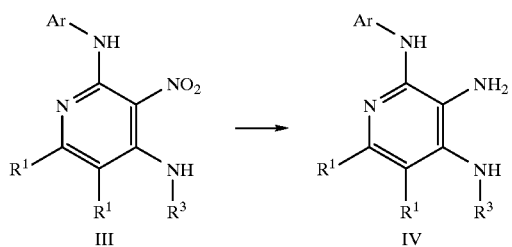

c. treating the compound of formula IV with diazotization and cyclization reagents to produce a compound of formula V or a mixture of a compound of formula V and a compound of formula VI;

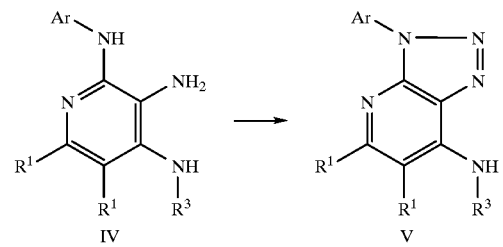

d. treating the compound of formula V or mixture of compounds of formulas V and VI with a base to convert the compound of formula V to the compound of formula VI

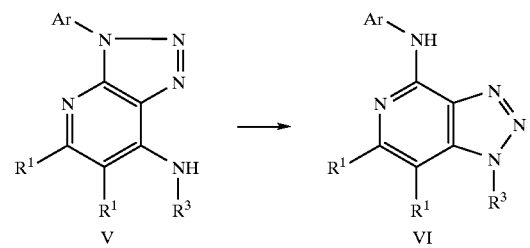

wherein in formulas I–VI:
Ar is independently at each occurrence selected from phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl and pyrazolyl, each optionally substituted with 1 to 5 $R^5$ groups;

$R^1$ is independently at each occurrence selected from H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH and —$S(O)_nR^{12}$;

$R^3$ is independently at each occurrence selected from H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, —$CONR^6R^7$, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$ and —$CONR^6R^7$;

$R^5$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —CO($NOR^9$)$R^7$, $CO_2R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^8COR^7$, —$NR^8CO_2R^7$, —$COR^7$ —$OR^7$, —$CONR^6R^7$, $CO_2R^7$, —CO($NOR^9$)$R^7$ and —$S(O)_nR^7$;

$R^6$ and $R7$ are independently at each occurrence selected from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is independently at each occurrence selected from H, $C_1$–$C_4$ alkyl, $C_1$–$C_4$ haloalkyl and $C_3$–$C_6$ cycloalkyl;

$R^{12}$ is $C_1$–$C_4$ alkyl or $C_1$–$C_4$ haloalkyl;

$R^{13}$ is independently at each occurrence selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, triazolyl, tetrazolyl and indazolyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$ and —$CONR^6R^7$; and n is independently at each occurrence 0, 1 or 2.

2. A method of claim 1 wherein in formulas I through VI:

Ar is phenyl or pyridyl, each optionally substituted with 1 to 3 $R^5$ groups;

$R^1$ is independently at each occurrence selected from H, $C_1$–$C_4$ alkyl, halo, CN, $C_1$–$C_4$ haloalkyl, —$NR^9R^{10}$, —$OR^{11}$ and —$S(O)_nR^{12}$;

$R^3$ is independently at each occurrence selected from H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, —$S(O)_nR^{13}$, —$CO_2R^7$, —$NR^8COR^7$, —$NR^8CONR^6R^7$, —$NR^8CO_2R^{13}$, —$NR^6R^7$, aryl and heteroaryl, where the aryl or heteroaryl is optionally substituted with 1 to 3 substituents independently selected at each occurrence from $C_1$–$C_4$ alkyl, halo, cyano, —$OR^7$, —$S(O)_nR^7$, —$CO_2R^7$, —$NR^8COR^7$, —$NR^8CONR^6R^7$, —$NR^8CO_2R^7$ and —$NR^6R^7$;

$R^5$ is independently at each occurrence selected from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, —$NO_2$, halo, —CN, $C_1$–$C_4$ haloalkyl, —$NR^6R^7$, $COR^7$ —$OR^7$, —$CONR^6R^7$, —CO($NOR^9$)$R^7$, $CO_2R^7$ and —$S(O)_nR^7$, where $C_1$–$C_6$ alkyl, $C_2$–$C_6$ alkenyl, $C_2$–$C_6$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, $COR^7$, —$OR^7$, —$CONR^6R^7$, —CO($NOR^9$)$R^7$ and —$S(O)_nR^7$;

$R^6$ and $R7$ are independently at each occurrence selected from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is independently at each occurrence selected from H, $C_1$–$C_4$ alkyl, $C_1$–$C_4$ haloalkyl and $C_3$–$C_6$ cycloalkyl;

$R^{12}$ is $C_1$–$C_4$ alkyl or $C_1$–$C_4$ haloalkyl;

$R^{13}$ is independently at each occurrence selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl and heteroaryl($C_1$–$C_4$ alkyl)-;

aryl is phenyl or naphthyl optionally substituted with 1 to 3 substituents independently selected at each occurrence from $C_1$–$C_4$ alkyl, halo, cyano, —$OR^7$, —$S(O)_nR^{12}$, —$CO_2R^8$, —$NR^8COR^7$, —$NR^8CONR^6R^7$, —$NR^8CO_2R^{12}$, and —$NR^6R^7$;

heteroaryl is independently at each occurrence selected from pyridyl, pyrimidinyl, triazinyl, furanyl, thienyl, imidazolyl, thiazolyl, indolyl, pyrrolyl, oxazolyl, isoxazolyl, pyrazolyl, triazolyl, tetrazolyl and indazolyl, each optionally substituted with 1 to 3 substituents independently selected at each occurrence from $C_1$–$C_4$ alkyl, halo, cyano, —$OR^7$, —$S(O)_nR^{12}$, —$CO_2R^8$, —$NR^8COR^7$, —$NR^8CONR^6R^7$, —$NR^8CO_2R^{12}$ and —$NR^6R^7$; and n is independently at each occurrence 0, 1 or 2.

3. The method of claim 1 for producing compound 6 comprising:

a. reacting compound 1 with compound 2 to produce compound 3

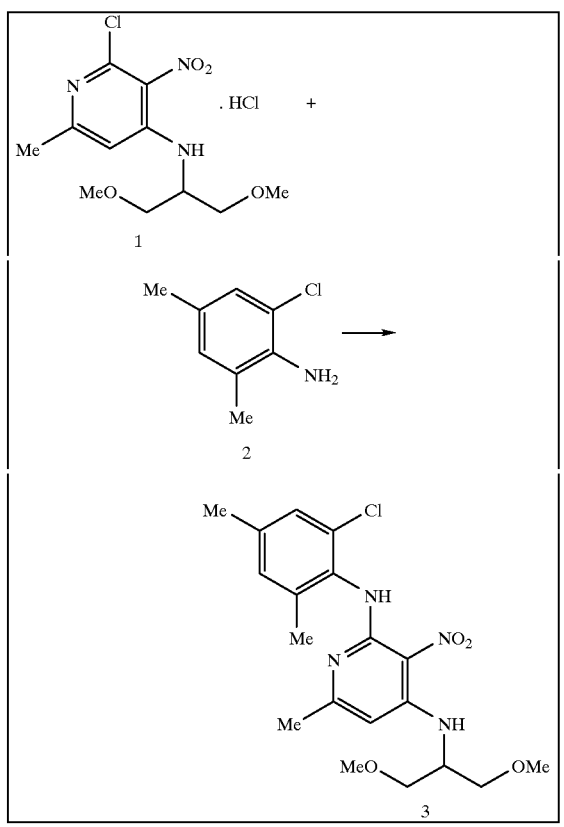
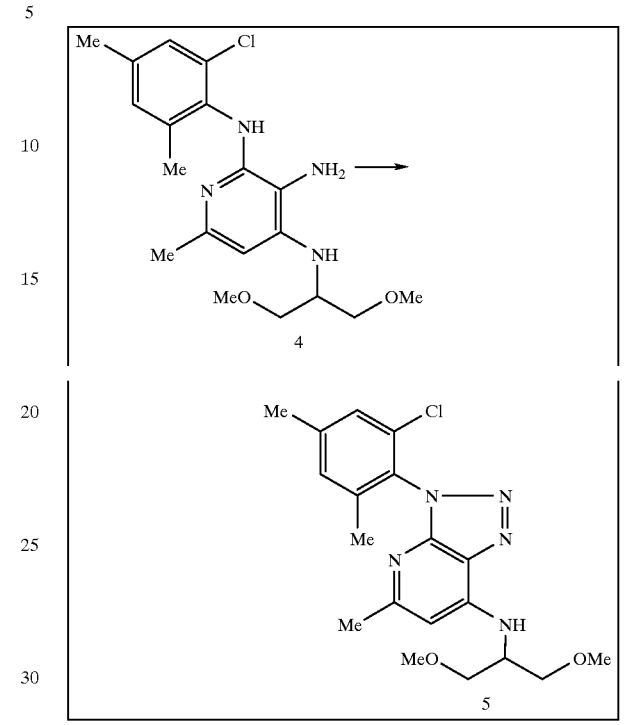
c. treating compound 4 with diazotization and cyclization reagents to produce compound 5 or a mixture of compound 5 and compound 6
b. treating compound 3 with a reducing agent to produce compound 4
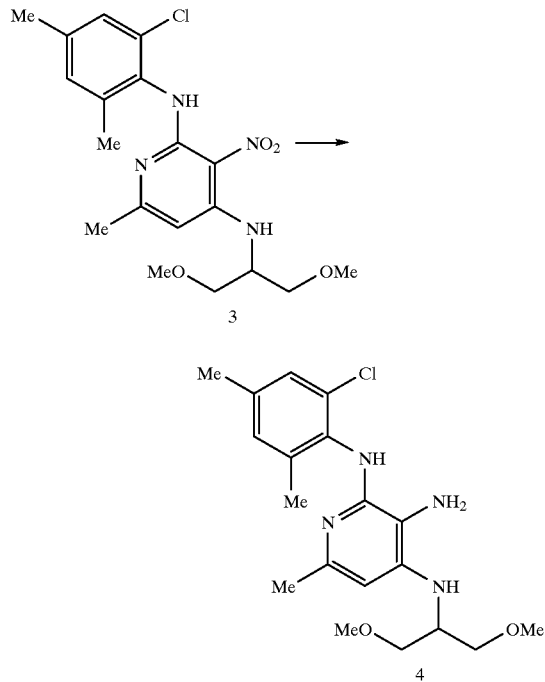
d. treating compound 5 or mixture of compounds 5 and 6 with a base to convert compound 5 to compound 6
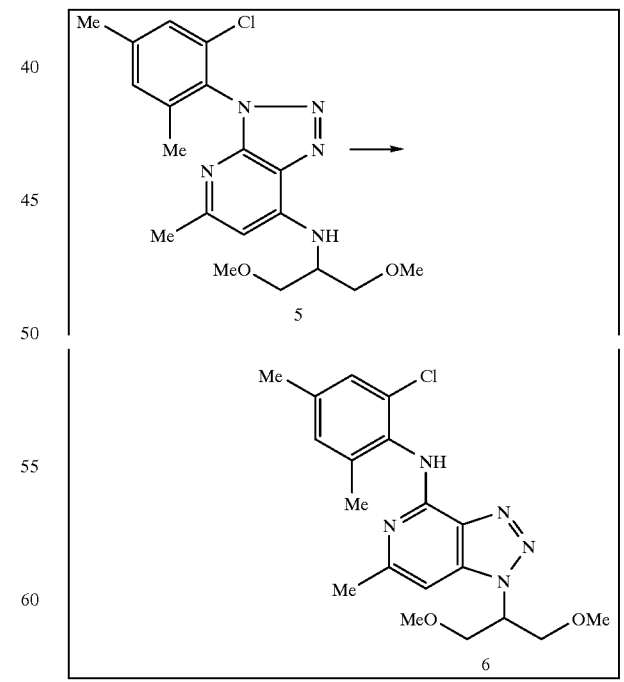

4. A method of making a compound of formula VI

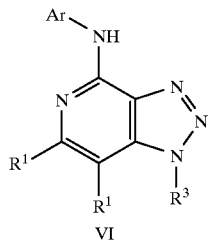

VI which comprises treating a compound of formula V or mixture of compounds of formulas V and VI with a base to convert the compound of formula V to the compound of formula VI

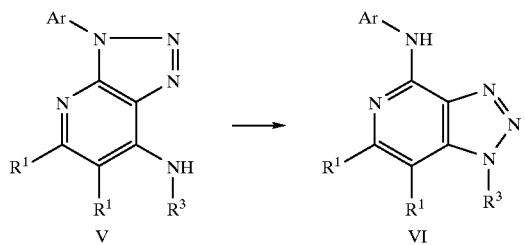

wherein in formulas V–VI:
Ar is independently at each occurrence selected from phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl and pyrazolyl, each optionally substituted with 1 to 5 $R^5$ groups;

$R^1$ is independently at each occurrence selected from H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH and —$S(O)_nR^{12}$;

$R^3$ is independently at each occurrence selected from H, $C_1$–$C_{10}$ alkyl, $C_2$–$C_{10}$ alkenyl, $C_2$–$C_{10}$ alkynyl, $C_3$–$C_8$ cycloalkyl and $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, —$CONR^6R^7$, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$ and —$CONR^6R^7$;

$R^5$ is independently at each occurrence selected from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —CO($NOR^9$)$R^7$, $CO_2R^7$ and —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^8COR^7$, —$NR^8CO_2R^7$, —$COR^7$ —$OR^7$, —$CONR^6R^7$, $CO_2R^7$, —CO($NOR^9$) $R^7$ and —$S(O)_nR^7$;

$R^6$ and R7 are independently at each occurrence selected from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence selected from H and $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is independently at each occurrence selected from H, $C_1$–$C_4$ alkyl, $C_1$–$C_4$ haloalkyl and $C_3$–$C_6$ cycloalkyl;

$R^{12}$ is $C_1$–$C_4$ alkyl or $C_1$–$C_4$ haloalkyl;

$R^{13}$ is independently at each occurrence selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl ($C_1$–$C_4$ alkyl)-, heteroaryl and heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$ and —$CONR^6R^7$;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, isoxazolyl , pyrazolyl, triazolyl, tetrazolyl and indazolyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$ and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —OC(O)$R^{13}$, —$NR^8COR^7$, —$N(COR^7)_2$, —$NR^8CONR^6R^7$, —$NR^8CO_2R^{13}$, —$NR^6R^7$ and —$CONR^6R^7$; and n is independently at each occurrence 0, 1 or 2.

5. The method of claim 4 for making the compound 6 by treating compound 5 or mixture of compounds 5 and 6 with a base to convert compound 5 to compound 6